(12) United States Patent
Wang et al.

(10) Patent No.: US 8,148,294 B2
(45) Date of Patent: Apr. 3, 2012

(54) METAL-POLYMER COMPOSITES COMPRISING NANOSTRUCTURES AND APPLICATIONS THEREOF

(75) Inventors: Hsing-Lin Wang, Los Alamos, NM (US); Sea Ho Jeon, Dracut, MA (US); Nathan H. Mack, Los Alamos, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 0 days.

(21) Appl. No.: 13/196,735

(22) Filed: Aug. 2, 2011

(65) Prior Publication Data
US 2011/0293820 A1    Dec. 1, 2011

Related U.S. Application Data

(62) Division of application No. 12/543,640, filed on Aug. 19, 2009, now Pat. No. 7,988,887.

(51) Int. Cl.
*B01J 23/48* (2006.01)

(52) U.S. Cl. ........ 502/347; 502/344; 977/700; 977/810; 356/301

(58) Field of Classification Search .................. 977/700, 977/810; 356/301; 502/347, 344; 252/512, 252/514
See application file for complete search history.

*Primary Examiner* — David W Wu
*Assistant Examiner* — Vu A Nguyen
(74) *Attorney, Agent, or Firm* — Bruce H. Cottrell; Meredith H. Schoenfeld

(57) ABSTRACT

Metal-polymer composites, and methods of making and use thereof, said composites comprising a thermally-cured dense polyaniline substrate; an acid dopant; and, metal nanostructure deposits wherein the deposits have a morphology dependent upon the acid dopant.

14 Claims, 11 Drawing Sheets

METAL-POLYMER COMPOSITES COMPRISING NANOSTRUCTURES AND APPLICATIONS THEREOF

CROSS REFERENCE TO RELATED APPLICATION

This application is a divisional of U.S. patent application Ser. No. 12/543,640 filed Aug. 19, 2009, which is a continuation-in-part of U.S. patent application Ser. No. 11/653,004, filed Jan. 11, 2007.

STATEMENT REGARDING FEDERAL RIGHTS

This invention was made with government support under Contract No. DE-AC52-06NA25396 awarded by the U.S. Department of Energy. The government has certain rights in the invention.

FIELD OF THE INVENTION

The present invention relates to metal-polyaniline composites, e.g., nanostructured metal-polyaniline composites, and to methods of preparation thereof.

BACKGROUND OF THE INVENTION

In the past few decades, there has been an increasing interest in using conducting polymers to fabricate electronic or optical devices such as light-emitting diodes and molecular electronics. Polyaniline (PANI) has been one of the most commonly used conducting polymers due to its facile synthesis, low cost and environmental stability, and has been carefully examined for use in electromagnetic shielding and anti-corrosion coatings.

PANI possesses secondary and tertiary amines in the backbone structure that can reversibly bind metal ions. In cases where metal ions have a reduction potential higher than that of the PANI, the bound metal ions can be reduced to form zero-valent metals. Thus, it has been recognized that PANI can be used for the electrodeless deposition of metals from a metal ion solution.

When suitable acid dopants are used during the deposition of metals onto a surface, unique nanostructures may be formed which correlate to the type of acid dopant. Surprisingly, it was found that these metal, nanostructure-PANI composites were useful substrates for SERS (Surface Enhanced Raman Spectoscopy), and provided not only significantly increased sensitivity, but an inexpensive alternative to available substrates. Previous work employed an asymmetric, porous PANI substrate. It is desirable, however, to also be able to deposit metal nanostructures onto thermally-treated, dense PANI films, as such films are more easily obtained by thermally evaporating the solvent.

Previously, it was not thought that nanostructures could be successfully produced on dense film substrates. As described in U.S. patent application Ser. No. 11/653,004, the use of PANI porous asymmetric membranes for the chemical deposition of metal layers, e.g., nanostructured metal layers has an advantage of lower density. as compared to thermally cured dense PANI films. The lower density is thought to allow diffusion of metal ions between PANI chains, which may aid the nucleation process. Furthermore, the phase inversion process used to prepare the PANI membranes does not involve heat treatment for a prolonged time period. The phase inversion process allows PANI to maintain its original redox states and is believed to minimize crosslinking between PANI chains.

Previous attempts at growing metal nanostructures on non-porous substrates resulted in different metal morphologies as compared to those grown on porous asymmetric membranes. The growth of metals on the thermally cured dense films exhibited less variation in their morphologies. In general, silver growth on top of a series of thermally cured PANI dense films exhibited large microstructures with random morphologies. After further research, however, it has surprisingly been found that metal nanostructures having reproducible morphologies can be produced on non-porous substrates which are useful for a variety of applications, including SERS.

SUMMARY OF THE INVENTION

The present invention describes thermally treated, dense PANI films having a variety of nanostructures on the surface, and methods for controllably depositing the nanostructures.

The following describe some non-limiting embodiments of the present invention.

According to a first embodiment of the present invention, a method of forming a metal-polymer composite is provided, comprising providing a thermally-cured dense polyaniline substrate; contacting the thermally-cured dense polyaniline substrate with an acid dopant to form a doped substrate; providing a solution comprising a metal ion; and contacting the solution comprising a metal ion with the doped substrate, whereupon metal nanostructure deposits are formed on the doped substrate, wherein the deposits have a morphology which is dependent upon the acid dopant.

According to another embodiment of the present invention, a method of forming a metal-polymer composite is provided, comprising providing a thermally-cured dense polyaniline substrate; providing a solution comprising a metal ion and an acid dopant; and contacting the solution comprising the metal ion and acid dopant with the thermally-cured dense polyaniline substrate, whereupon metal nanostructure deposits are formed on the doped substrate, wherein the deposits have a morphology which is dependent upon the acid dopant.

According to yet another embodiment of the present invention, a method of performing surface-enhanced Raman spectral analysis of an analyte is provided, comprising providing a thermally-cured dense polyaniline substrate, wherein a surface of the substrate comprises metal nanostructure deposits and an acid dopant; bringing an analyte into effective contact with said metal-PANI composite; illuminating the metal-PANI composite with radiation of at least one wavelength for causing elemental-state particles to produce a plasmon field and for causing said plasmon field to interact with molecules of said analyte, in such a manner, so as to produce Raman photons; and, collecting scatted radiation emitted, from said metal-PANI composite for spectral analysis.

According to yet another embodiment of the present invention, a metal-polymer composite is provided, comprising a thermally-cured dense polyaniline substrate; an acid dopant; and, metal nanostructure deposits wherein the deposits have a morphology dependent upon the acid dopant.

BRIEF DESCRIPTION OF THE DRAWINGS

In all Figures, the x-axis represents wavelength in $cm^{-1}$ and the y-axis represents signal intensity

FIGS. 8 (a)-(b) show a SERS spectrum of mercaptobenzoic acid (MBA) (a) obtained from a silver nanostructure of the present invention made with 20 mM silver nitrate and doped with mandelic acid, and the corresponding SEM image of the nanostructure (b).

FIGS. 9 (a)-(b) show a SERS spectrum of mercaptobenzoic acid (MBA) (a) obtained from a silver nanostructure of the present invention made with 20 mM silver nitrate and doped with p-toluene sulfonic acid, and the corresponding SEM image of the nanostructure (b).

FIGS. 10 (a)-(b) show a SERS spectrum of mercaptobenzoic acid (MBA) (a) obtained from a silver nanostructure of the present invention made with 20 mM silver nitrate and doped with polystyrene sulfonic acid, and the corresponding SEM image of the nanostructure (b).

DETAILED DESCRIPTION

The present invention is concerned with the metal-polyaniline composites comprising a dense-film PANI substrate, and to methods of producing these metal-polyaniline composites, wherein the metal forms various nanostructures on the surface of the composite. The present invention is also concerned with the use of such metal-polyaniline composites, e.g., such nanostructured metal-polyaniline composites, in applications employing Surface Enhanced Raman Scattering (SERS).

"Thermally-cured dense polyaniline substrate," as used herein, means a substrate made according to a method comprising the steps of spreading the polymer solution onto a solid surface into a wet film and heating to a specified temperature, and is understood not to include polyaniline substrates that are formed and/or combined with a metal ion in solution.

"Morphology dependent upon the acid dopant," as used herein, means that a particular add dopant reproducibly results in a specific morphology when applied under conditions specified herein with respect to acid dopant concentration, metal concentration, identity of the metal, time of immersion, etc.

The substrates of the present invention are dense-film substrates, which are comprised of a single, substantially uniform layer of a conductive polymer such as PANI. In contrast to asymmetric porous PANI membranes, which are produced by a solvent exchange process, production of the substrates of the present invention requires thermal treatment. The substrates of the present invention are understood not to include substrates formed by mixing a metal ion and a polymer in solution, but rather, the metal is grown in situ after formation of the substrate.

In the present invention, metal-polyaniline composites are prepared by growing the metal particles on the substrate in situ, as opposed to depositing pre-formed metal structures onto a substrate. In contrast to currently available SERS substrates, which are small in size and expensive to produce, the method of the present invention is suitable for inexpensively producing composites that in theory may be of any size ranging from a square millimeters to square meters. The composites may be prepared by electrodeless deposition. The reduction potential of PANI at its emeraldine base form versus a standard reference hydrogen electrode is from about 0.70 V to 0.75 V whereas PANI at its leucoemeraldine base form versus a standard reference hydrogen electrode is from about 0.30 V to 0.40 V. Where the particular metal ions have a reduction potential greater than that of the PANI, immersion of a suitable PANI film or membrane into an aqueous solution of the particular metal ions can result in the deposition of metal upon the PANI and form the metal-PANI composite. For silver nitrate (reduction potential of 0.8 V), gold chloride (reduction potential of 1.5 V), and platinum chloride (reduction potential of 0.755 V), a metal coating including metal nanoparticies can form upon a PANI porous asymmetric membrane or thermally cured PANI dense film dipped into the aqueous metal salt solution. Metals useful in the composite structures of the present invention can generally include metals such as gold, silver, platinum, palladium and the like.

Conducting polymers suitable for use in the present invention include conducting polymers such as polyaniline (PANI), polypyrrole, polythiophene, poly(phenylene vinylene), and combinations thereof. In one embodiment, the conducting polymer is polyaniline.

Polyaniline is the name given to the polymer having the structure, in a completely reduced leucoemeraldine oxidation state, of the general formula:

where n is greater than 5 and where R is a hydrogen atom. Alternatively, R may be a substituent such as an organic group, including, for example, $CH_3$, $C_2H_5$, $OCH_3$, $N(CH_3)_2$, an inorganic group, including, for example, F, Cl, Br, I, or a metal chelate group. For the polyanilines described herein, the appropriate choice of an R group permits a greater range of solubility in a greater number of different types of solvents, which results in increased versatility for processing the polymers and a greater range of chemical properties.

In situ deposition of metals on top of PANI surfaces can be achieved by immersing thermally cured dense PANI films into an aqueous metal ion solution with a wide range of metal ion concentrations. In one embodiment, the metal ion concentration ranges from about 0.001 Molar (M) to about 1.0 M. The time period necessary for the metal growth ranges from about several seconds to about several hours depending upon the experimental conditions such as temperature and metal ion concentration. The membranes are typically left in solution until metal deposition can he observed visually on the target surface.

In one embodiment of the present invention, the aqueous solution comprising the metal is first doped with a suitable acid, and a suitable substrate is then immersed in the aqueous solution. In an alternative embodiment, the substrate is provided and doped with a suitable acid. The doped membranes are then immersed into the aqueous solution comprising the metal. The morphology and size of the nanostructures is dependent upon, and correlates to, the identity of the acid dopant. Suitable acid dopants include, but are not limited to, hydrochloric acid (HCl), tartaric acid, camphosulfonic acid, phosphoric acid ($H_3PO_4$), trifluoroacetic acid ($CF_3COOH$), citric acid (2-hydroxypropane-1,2,3-tricarboxylic acid), mandelic acid (2-phenyl-2-hydroxyacetic acid), poly(styrene sulfonic acid), para-tolueriesulfonic acid ($p-CH_3C_6H_5SO_3H$), and combinations thereof. The resulting deposited metal nanostructures exhibited varying morphologies as seen in FIGS. 1-11.

Figure 1:
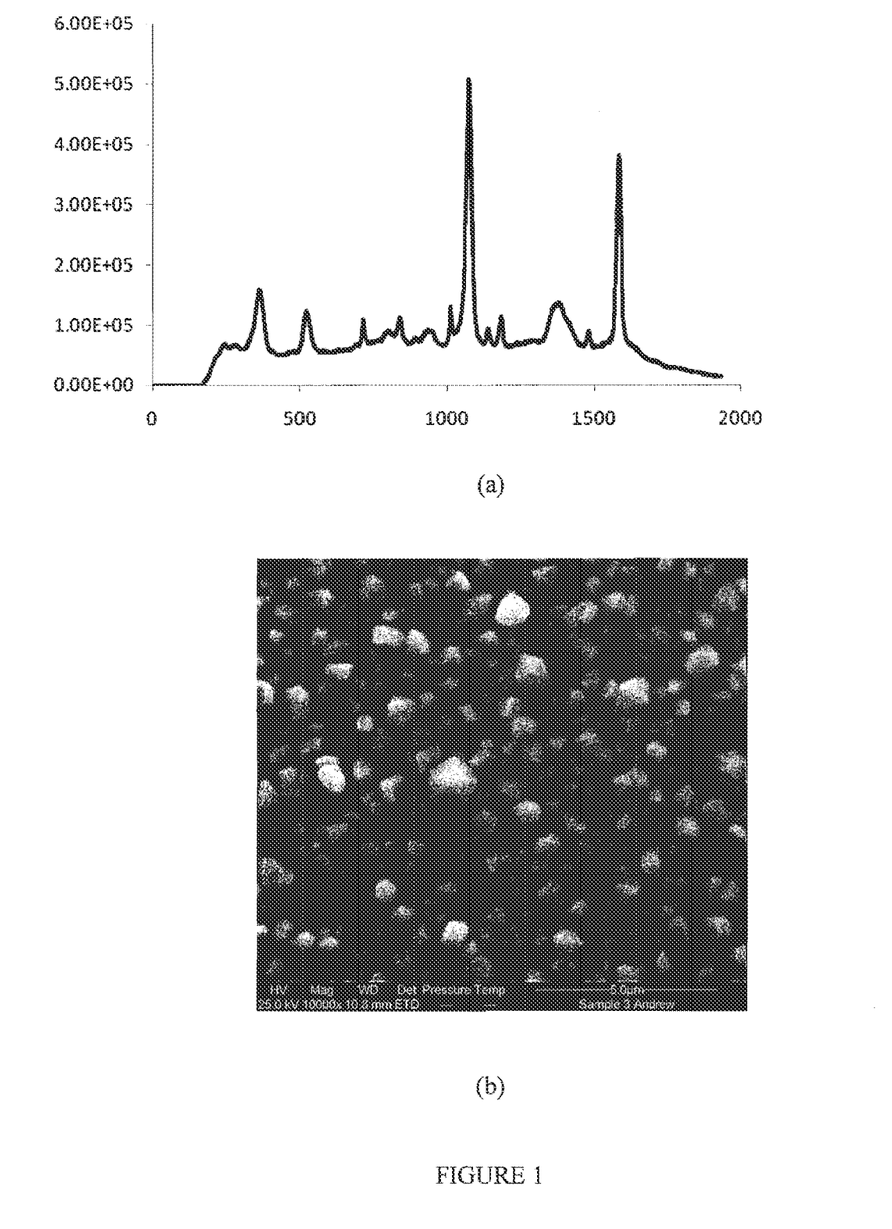
FIGS. 1(a)-(b) show a SERS spectrum of mercaptobenzoic acid (MBA) (a) obtained from a silver nanostructure of the present invention made with 1 mM silver nitrate and doped with citric acid, and the corresponding SEM image of the nanostructure (b).
Figure 2:
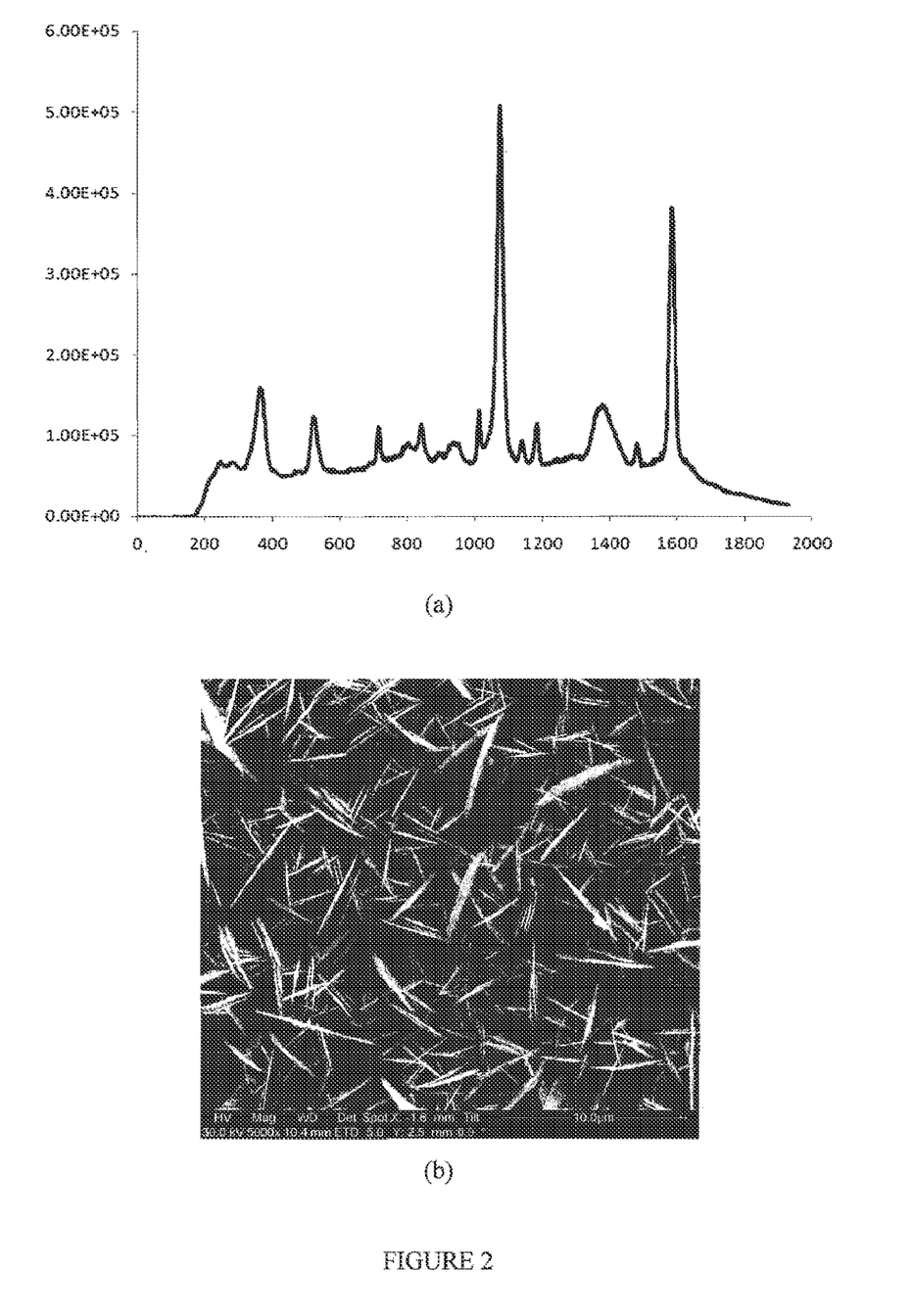
FIGS. 2(a)-(b) show a SERS spectrum of mercaptobenzoic acid (MBA) (a) obtained from a silver nanostructure of the present invention made with 10 mM silver nitrate, and the corresponding SEM image of the nanostructure (b). PANI dense film shown in (a); and, (d) the silver coated HCl doped PANI dense film shown in of the nanostructure (b).
Figure 3:
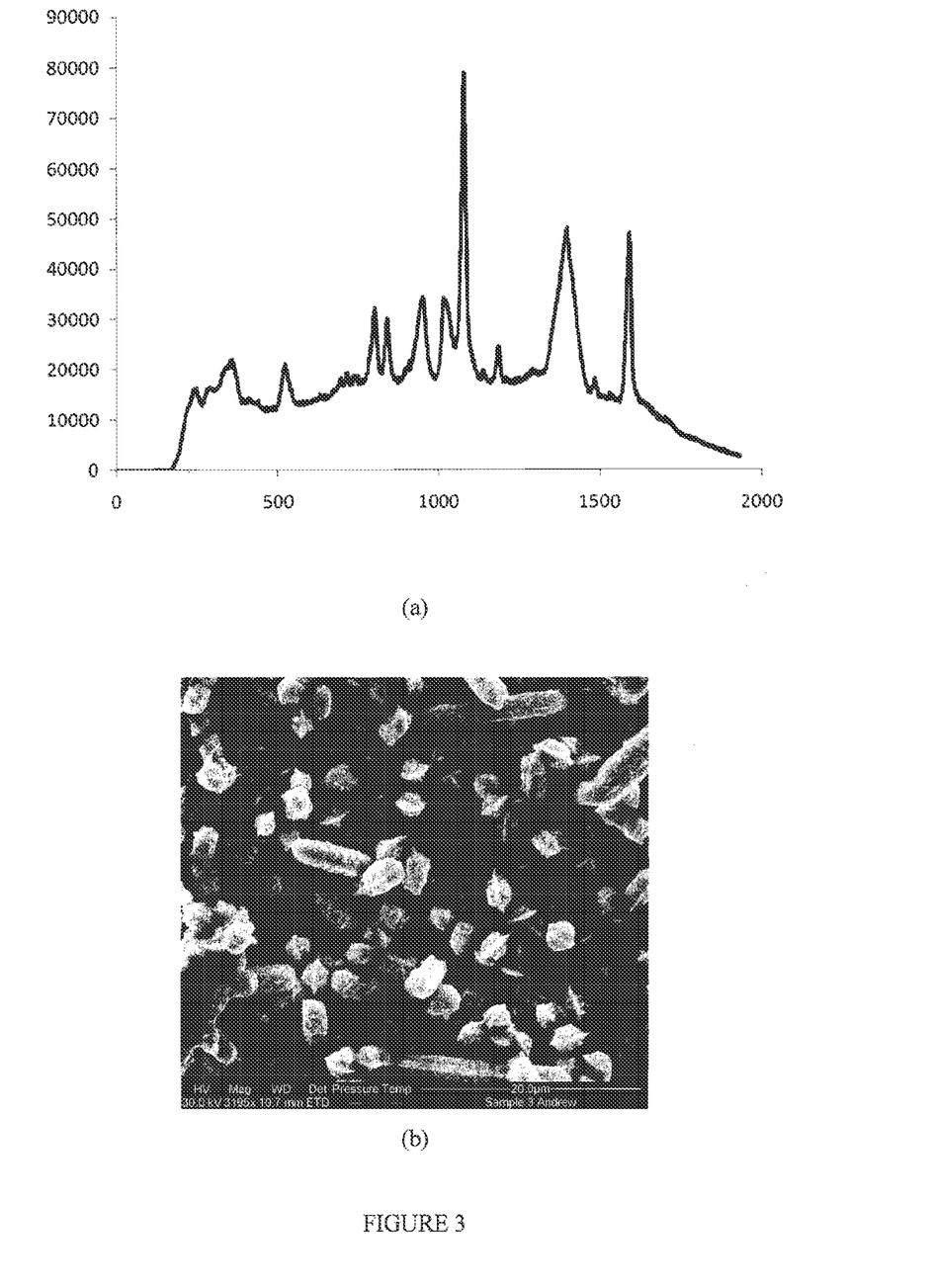
FIGS. 3(a)-(b) show a SERS spectrum of mercaptobenzoic acid (MBA) (a) obtained from a silver nanostructure of the present invention made with 20 mM silver nitrate and doped with citric acid, and the corresponding SEM image of the nanostructure (b).
Figure 4:
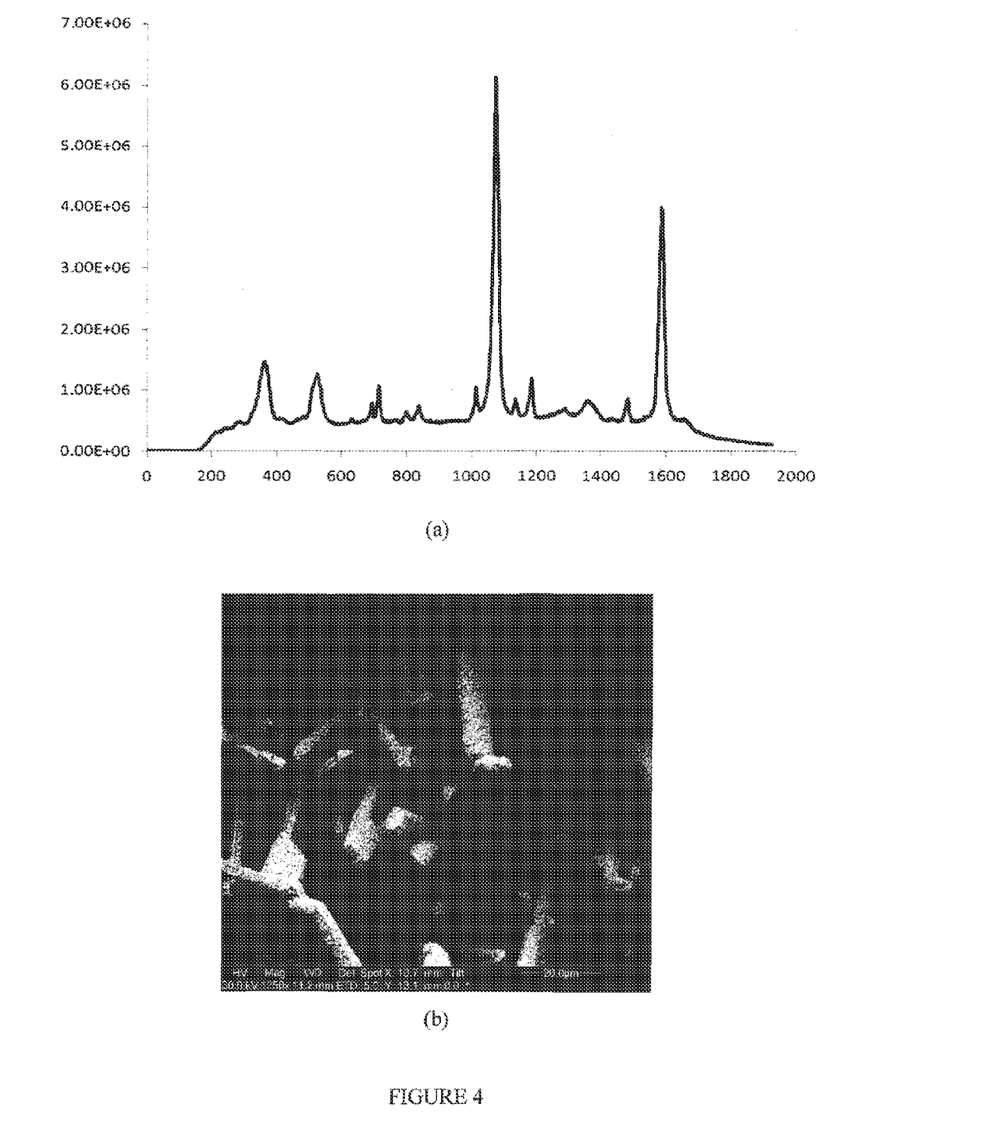
FIGS. 4(a)-(b) show a SERS spectrum of mercaptobenzoic acid (MBA) (a) obtained from a silver nanostructure of the present invention made with 100 mM silver nitrate and doped with citric acid, and the corresponding SEM image of the nanostructure (b).
Figure 5:
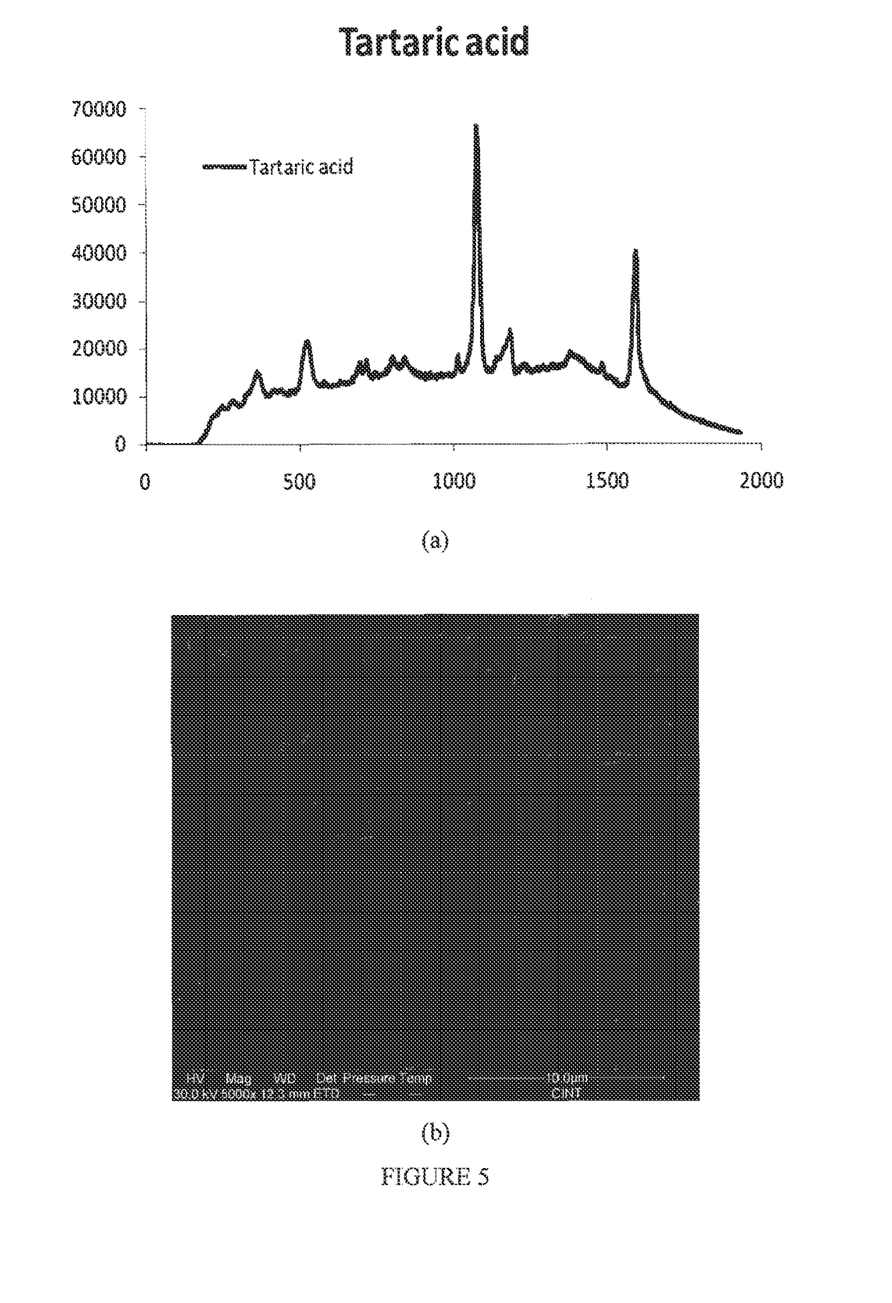
FIGS. 5(a)-(b) show a SERS spectrum of mercaptobenzoic acid (MBA) (a) obtained from a silver nanostructure of the present invention made with 20 mM silver nitrate and doped with tartaric acid, and the corresponding SEM image of the nanostructure (b).
Figure 6:
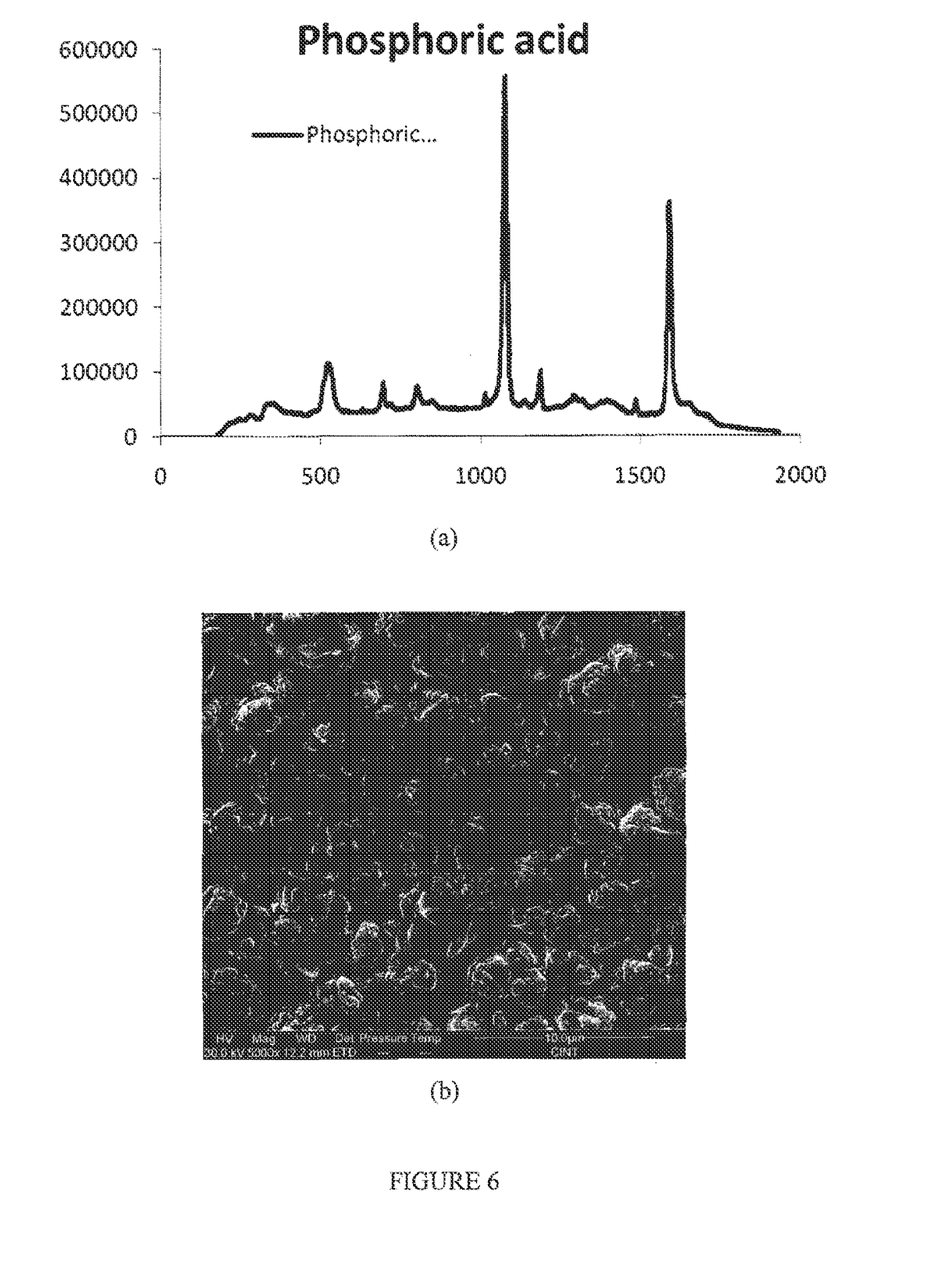
FIGS. 6(a)-(b) show a SERS spectrum of mercaptobenzoic acid (MBA) (a) obtained from a silver nanostructure of the present invention made with 20 mM silver nitrate and doped with phosphoric acid, and the corresponding SEM image of the nanostructure (b).
Figure 9:
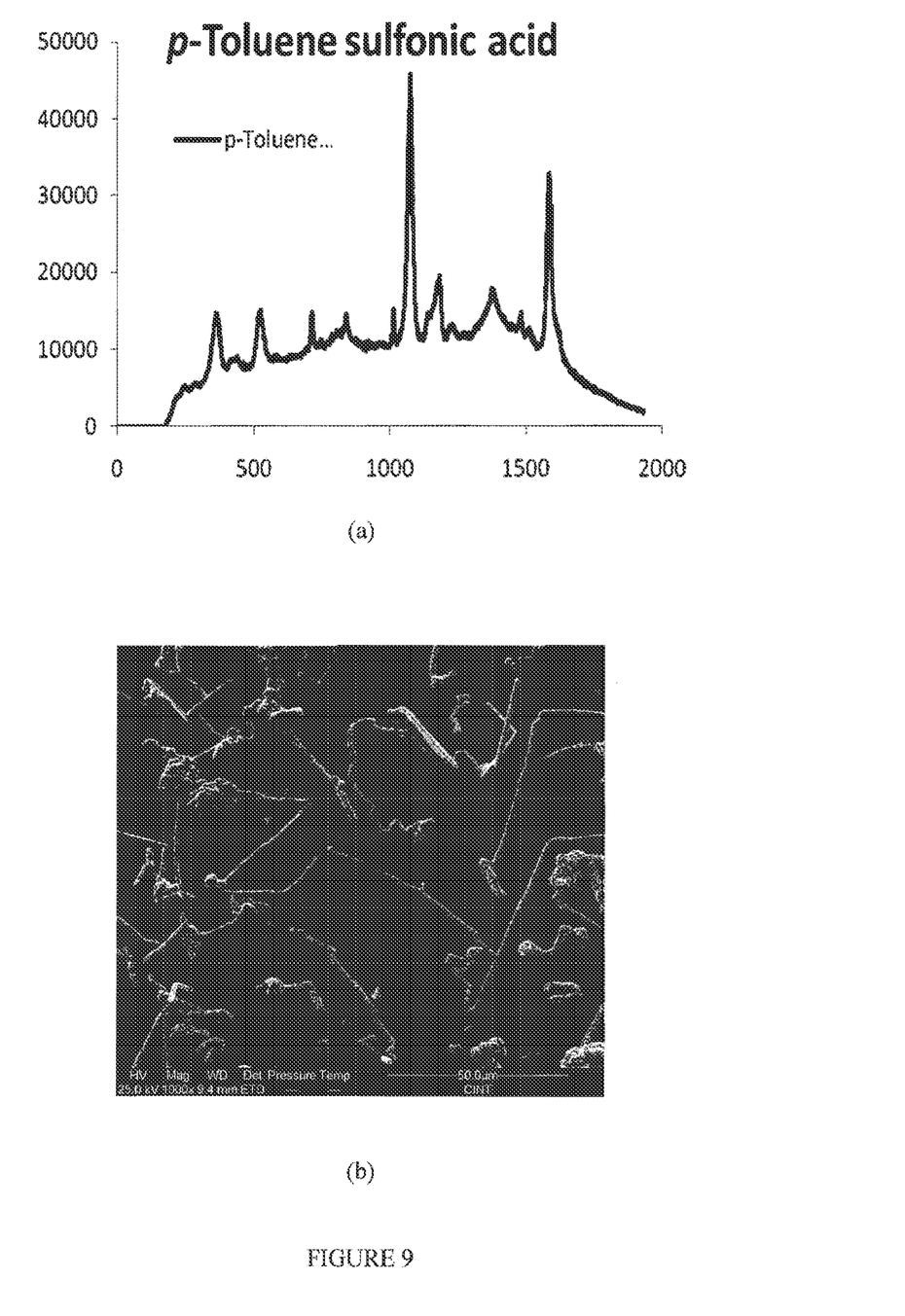
Figure 11:
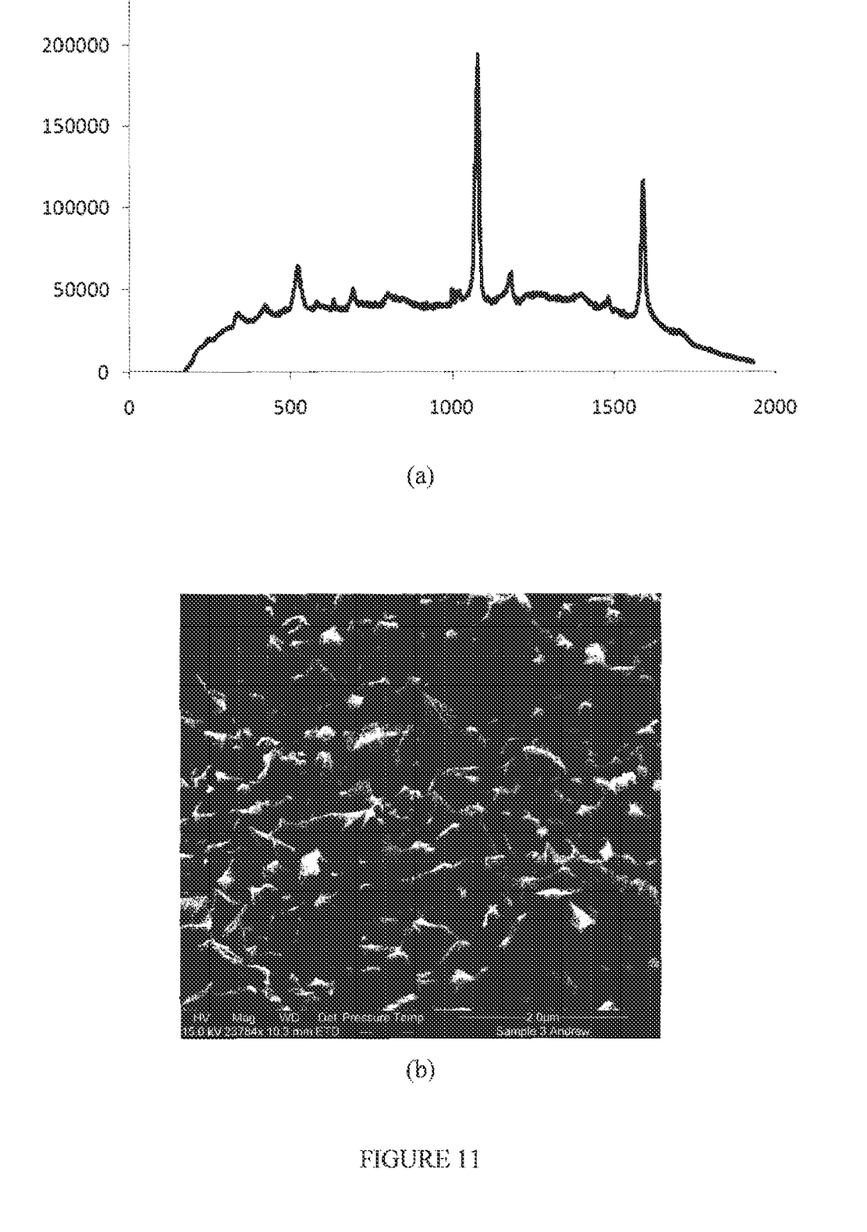
FIGS. 11(a)-(b) show a SERS spectrum of mercaptobenzoic acid (MBA) (a) obtained from a gold nanostructure of the present invention made with 200 mM $AuCl_3$ with HCl, and doped with citric acid, and the corresponding SEM image of the nanostructure (b).

The morpohologies of the nanostructures include sheets, cubes, sheres (e.g., sphere-like dots, as shown in FIGS. 1, 5 and 6), needles (e.g., needle-like structures, as shown in FIG. 2), rods (e.g., rod-like structures as shown in FIGS. 3 and 4), wires (e.g. as shown in FIG. 9), and random nanostructures (e.g., as shown in FIG. 11).

Metal deposition on the PANI membrane surfaces through reduction requires electron transfer from the PANI to the metal ions. As the metal ions approach the PANI membrane surface, they can be reduced by the PANI and form nuclei. In a conventional homogeneous system, where metal ions and a reducing agent are both dispersed in solution, the metal nuclei can serve as catalytic sites for subsequent surface growth allowing the formation of larger metal structures. The present invention involves a heterogeneous system. In such a heterogeneous system, metal ions are reduced on the PANT membrane surface itself and the growth mechanism can be expected to differ from a homogeneous system. While not wishing to he bound by the present explanation, the size of the metal nanoparticles is likely to be dominated, by the difference in reduction potential between metal ions and the PANI and by the surface properties, of the PANI membrane substrate. The morphological difference corresponding to the various dopants may be influenced by the surface energy of the PANI membrane. The surface energy of the PANI membrane, manifested by the water contact angles, can be tuned by the nature of the dopants and the redox states of the PANI membrane.

Figure 7:
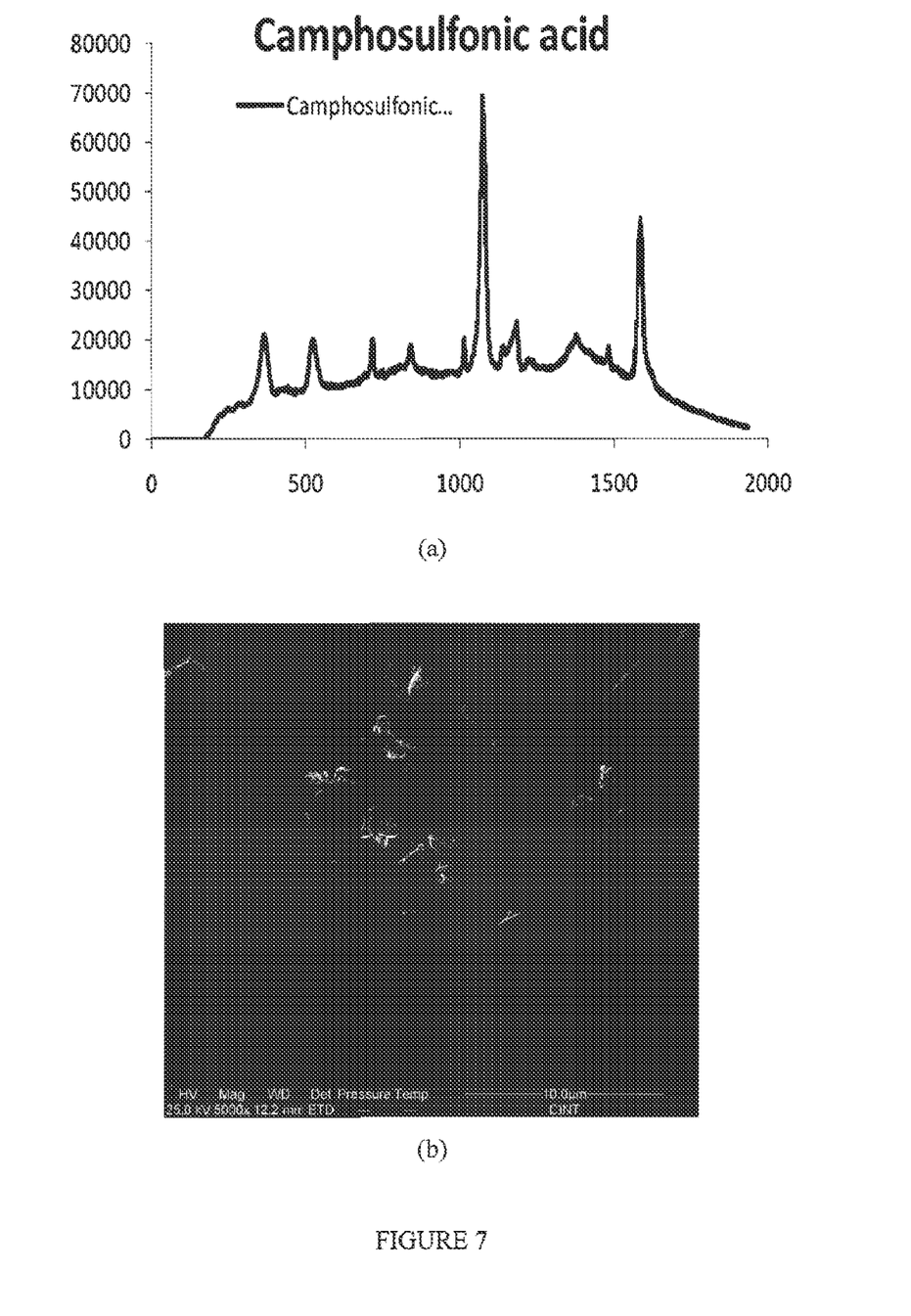
FIGS. 7(a)-(b) show a SERS spectrum of mercaptobenzoic acid (MBA) (a) obtained from a silver nanostructure of the present invention made with 20 mM silver nitrate and doped with camphosulfonic acid, and the corresponding SEM image of the nanostructure (b).
Figure 8:
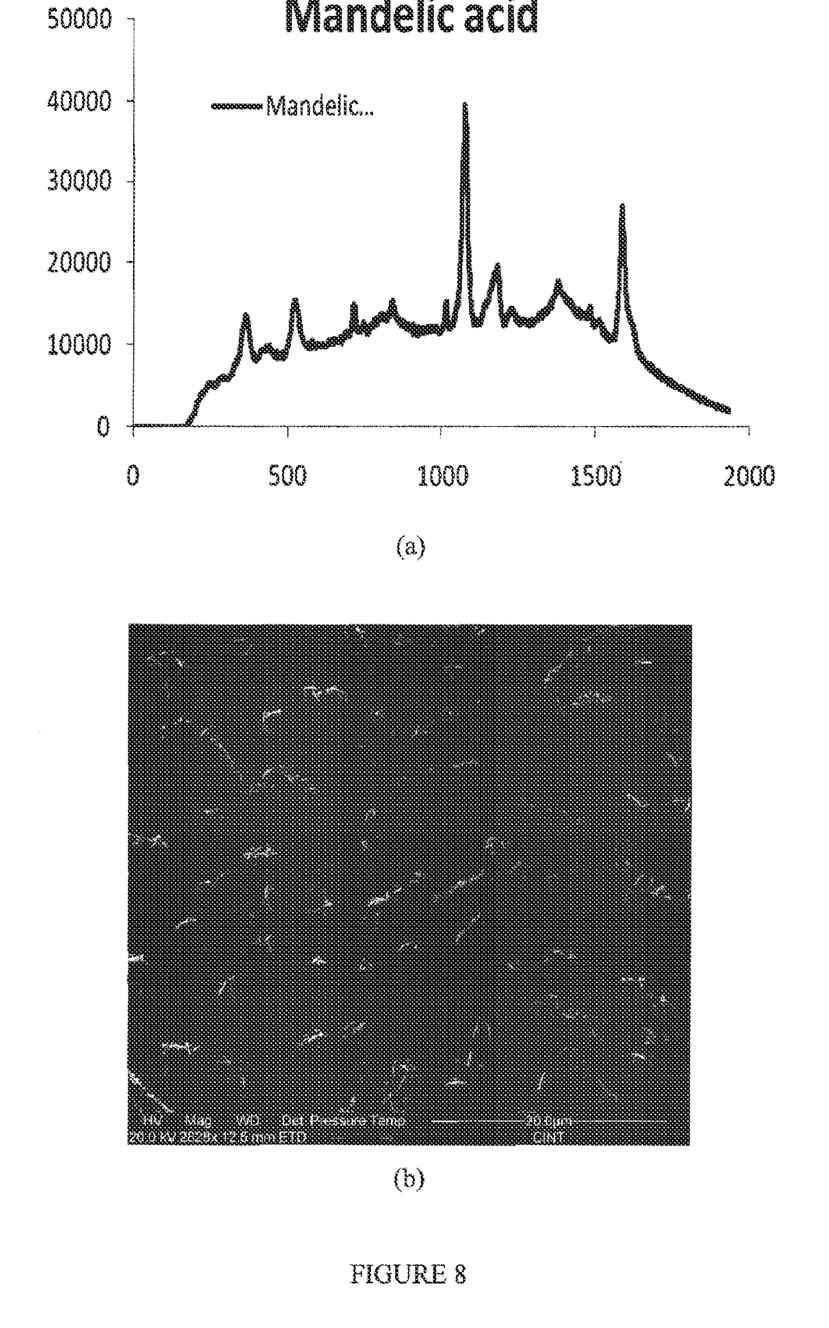

Control of metal growth could also be achieved by using a stretched PANI film (a thermally cured PANI dense film). The stretching of the PANI dense films can generally be from about 100 percent to 500 percent of the original size, more preferably from about 100 percent to about 400 percent of the original size. The contrast between silver deposited on the stretched and unstretched PANI dense film is shown in FIG. 7. A preferential deposition of the silver on the PANI dense film surface coincided with the stretched direction. In contrast, the unstretched PANI dense films exhibited homogeneous silver deposition throughout the PANI dense film surface. Without wishing to be limited by theory, such a preferential silver deposition is thought to result from the lower reduction potential of the stretched oriented PANI dense film. The stretched (extended) PNI chain conformation leads to formation of crystalline regions having lower reduction potential and higher conductivity that the unstretched film portions.

The metal-PANI composites of the present invention can provide good catalytic activity to various organic reactions especially toward hydrogenation reactions. As the metal., e.g., metal nanoparticles, are stably adfixed to the PANI membrane, it can be easily recycled and reused whereas typical commercially available metal catalysts, e.g., Pd on C, can only be used once.

In one embodiment, metal-PANI composites of the present invention wherein the metal is platinum or palladium can be used in the selective hydrogenation of alkenes and alkynes.

Surface roughness has been considered an important factor that governs SERS. It has been previously observed that molecules near roughened silver surfaces show enhanced Raman scattering of as much as two orders of magnitude or more. The ability to detect and identify trace amounts of chemicals has become increasingly important. SERS has proven to be one of the most sensitive methods for performing chemical analysis by the detection of a single molecule. SERS offers the advantage of trace detection by increasing the scattering light intensity by as much as a factor of $10^{10}$, especially with nanostructured metals such as silver and gold.

The SERS effect leads to a major increase of the Raman scattering cross-section for molecules absorbed onto suitably rough metal surfaces. Thus, use of the composites of the present invention in SERS applications has a large potential in analytical chemistry and for biological applications. The structures of the present invention result in an enhancement of the localized electric field, which subsequently increases the SERS from the metal particles in the composite structures.

Through the process of the present invention, the formation of metals on reductive PANI surfaces can be controlled by tailoring the surface chemistry and redox potential. A wide range of metal nanostructure morphologies can be achieved by selection of dopant. The sizes of the deposited metal structures could also be varied from a few nanometers to several microns. The composite materials of the present invention may further have application in surface processing, catalysis (e.g., in fuel cells or other chemical reactions), as modified surface electrodes, for anticorrosion and for biosensors.

The present invention is more particularly described in the following examples which are intended as illustrative only.

EXAMPLES

Reagents: N-Methyl-2-pyrrolidone (99% Aldrich), heptamethylenimine (HPMI, 98% Acros), citric acid (99.9% Fisher), silver nitrate (99.9999% Aldrich), hydrochloric acid (37%, Fisher), gold chloride (99%, Aldrich), 4-mercaptobenzoic acid (90%, Aldrich), and polyaniline emeraldine base (EB) powder (Aldrich) were used as received.

Microscopy: PANI membrane surfaces were imaged using either a JEOL 6300FXV SEM or a FEI Quanta FEG ESEM.

Spectroscopy: All metallic substrates were prepared for spectroscopic analysis by forming a self assembled monolayer of 4-mercaptobenzoic acid (MBA) on their surface. Each substrate was immersed in a 5% ethanolic solution of MBA for 1 hour and then rinsed with fresh ethanol three times and allowed to air dry. Surface enhanced Raman spectra (SERS) were recorded using approximately 1 mW, 785 nm. excitation focused onto the sample through a 0.5 NA microscope objective. The scattered Raman signal was collected in a backscattering configuration through the objective, filtered, and then dispersed onto a liquid nitrogen cooled CCD camera through a single grating spectrometer. All spectra were recorded using total integration times of 10 seconds.

PANI Starting Solution: Concentrated PANI solutions (2.0% w/w) were prepared as follows. First, 1.15 g of EB powder was mixed with 0.747 g of heptamethyleneimine (HPMI) in a 12 mL Teflon vial for ten minutes with a spatula. Then, 4.14 g of N-methyl-2-pyrrolidinone (NMP) was added and stirred with a spatula for 30 minutes until the visible solid PANI particles were dispersed. The PANI solution was then filtered through a 10 mL syringe using a cotton plug.

PANI Thin Films: The concentrated PANI solution was poured onto a glass substrate and smeared into a homogeneous thin film using a Gardner blade. The glass substrate and film were kept in a leveled oven at a 55° C. for two days to remove the solvents. The dried film was then detached from the glass substrate by immersing it in approximately 4 L water bath and then kept in the water bath overnight to ensure the removal of solvent residual (NMP and HPMI) by solvent exchange. The pristine PANI films were then dried in air for 1 hour, then sandwiched between two KimWipes, and placed under a flat metal weight (15 kg) for one day to keep the dry film flat. The resulting thermally cured, dense PANI film has a thickness of 1 µm-350 µm (as measured by micrometer or vernier calipers) depending on the thickness setting of the Gardner blade. The films were then doped by immersing them into an acid solution (typically in the concentration range from 0.01 M-0.25 M) for 24-144 hours followed by three rinses in 100 mL of purified water for 1-30 minutes.

Metal Nano Structures on PANI: The acid doped films were cut into 5×5 mm pieces and immersed into freshly prepared aqueous metal ion solutions (AgNO$_3$, or HAuCl$_4$ plus HCl) after which, metallic nanostructures immediately and spontaneously begin to form on the PANI surface. Rinsing the PAM film in water for 5 seconds halts all metal growth, and the metal structures are finally dried in air. Reaction conditions such as the PANI film thickness, the concentration of metal ion, and the total exposure time of the PANI film to the ion solution were all found to dramatically affect the resulting metal nanostructures.

Example 1

FIGS. 1-4 contains representative SEM images of silver nanostructures formed on a 350 µm thick citric acid doped PANI film and SERS spectra of silver nanostructures grown at each respective concentration. The silver structures were grown from silver nitrate solutions with concentrations of 1 mM (FIG. 1), 10 mM (FIG. 2), 20 mM (FIGS. 3), and 100 mM (FIG. 4). The morphology varies with increasing silver ion concentration ranges from featureless particles to nanosheet assembly to rod-like assemblies. All of these silver nanoparticles exhibit strong SERS activity manifested by the SERS spectra of mercaptobenzoic acid (MBA). The SERS signal is collected under 1 mW of laser power and a collection time of 10 secs.

Example 2

Figure 10:
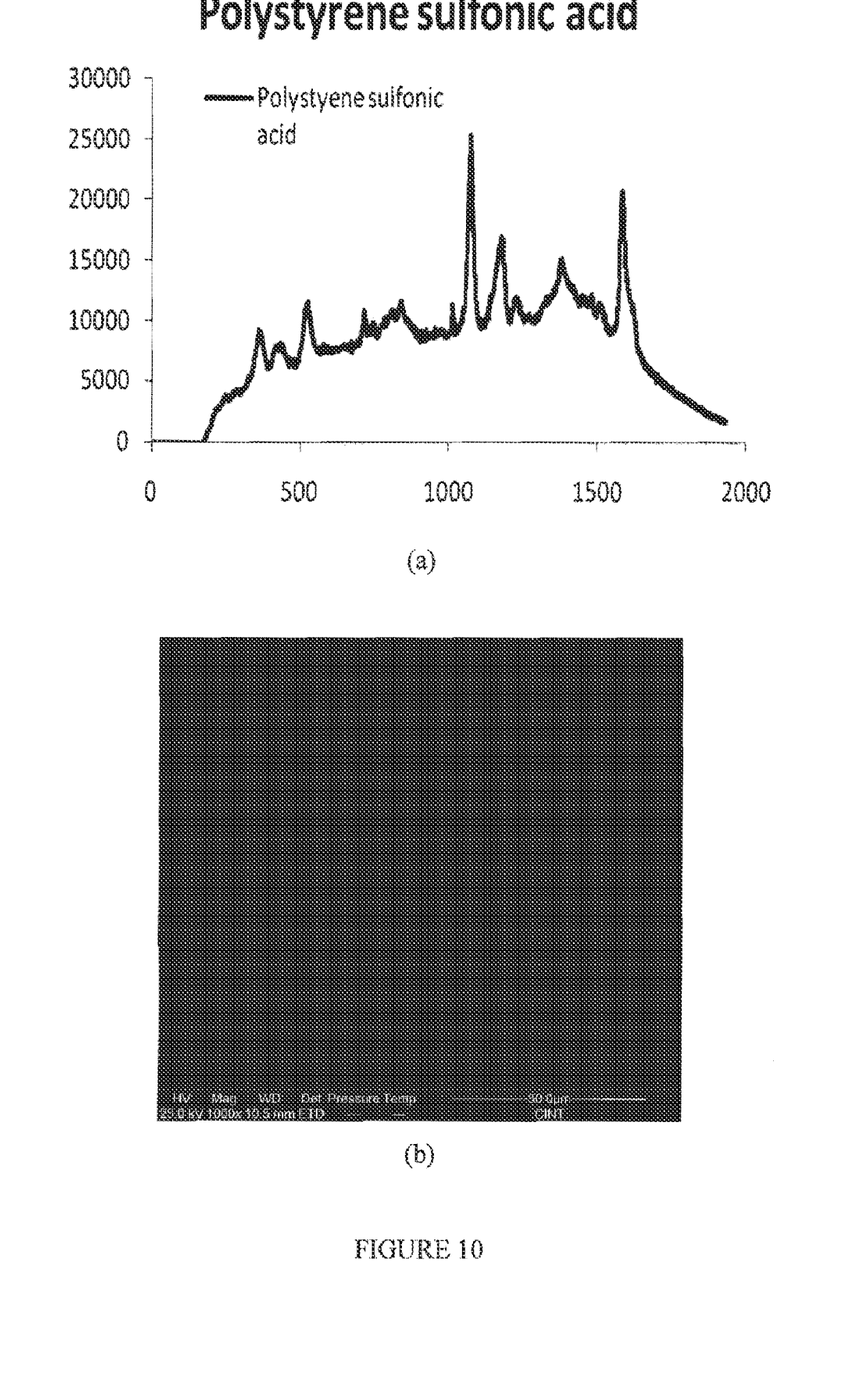

FIGS. 5-10 contain representative SEM images of silver nanostructures formed on a 150 µm PANI film which are doped with various acids having a pH of 1.5, and SERS spectra of silver nanostructures grown at 20 mM. The PANI film were doped in tartaric acid (FIG. 5), phosphoric acid (FIG. 6), camphosulfonic acid (FIG. 7), mandelic acid (FIG. 8), p-toluene sulfonic acid (FIG. 9), and poly(styrene sulfonic acid) (FIG. 10). The morphology of silver particles grown on PANI films is acid dependent. The morphology ranges from particles to wires. All of these silver nanoparticles exhibit SERS activity manifested by the SERS spectra of mercaptobenzoic acid (MBA). The SERS signal is collected under 1 mW of laser power and a collection time of 10 secs.

Example 3

FIG. 11 shows representative SEM images of gold nanostructures formed on a 150 µm PANI film. The gold structures were grown for overnight from a mixture, 2 mL of 200 mM AuCl$_3$ solution with 50 µL of 37% hydrochloric acid. The gold structure has some sharp edges. This Au particles exhibit SERS activity manifested by the SERS spectra of mercaptobenzoic acid (MBA). The SERS signal is collected under 1 mW of laser power and a collection time of 10 secs.

Example 4

The Ag particles grown on PANI films with different thickness ranges from 50 to 340 µm also show variation in morphology and they also show SERS activity that appears to be somewhat morphological dependent. This result suggests another way of controlling the particle morphology as well as their corresponding SERS activity.

Example 5

Ag particles were also grown on 150 µm thick undoped PANI films that were immersed in 1 ml of AgNO$_3$ solution (10 mM) containing a dopant (50 µl of citric acid—0.25 M). This simultaneous doping and deposition process results in Ag metal nanostructures very similar to those observed with pre-dopped PANI films. This co-doping/deposition method is general, and applies to any dopant of choice.

What is claimed is:

1. A method of forming a metal-polymer composite comprising:
    a) providing a thermally-cured dense polyaniline substrate;
    b) contacting the thermally-cured dense polyaniline substrate with an acid dopant to form a doped substrate;
    c) providing a solution comprising a metal ion; and
    d) contacting the solution comprising a metal ion with the doped substrate, whereupon metal nanostructure deposits are formed on the doped substrate, wherein the deposits have a morphology which is dependent upon the acid dopant.

2. The method of claim 1, wherein the metal is selected from the group consisting of silver and gold.

3. The method of claim 1, wherein the acid dopant is selected from the group consisting of tartaric acid, camphosulfonic acid, phosphoric acid, citric acid, mandelic acid, poly(styrene sulfonic acid), para-toluenesulfonic acid, and combinations thereof.

4. The method of claim 1, wherein the nanostructure deposits are sheets, cubes, spheres, needles, rods, or wires.

5. The method of claim 4, wherein the nanostructure deposits are wires.

6. The method of claim 1, wherein the metal is silver and the acid dopant is citric acid.

7. The method of claim 1, wherein the metal is silver, the acid dopant is para-toluenesulfonic acid, and the nanostructure deposits are wires.

8. A method of forming a metal-polymer composite comprising:
   a) providing a thermally-cured dense polyaniline substrate;
   b) providing a solution comprising a metal ion and an acid dopant; and
   c) contacting the solution comprising the metal ion and acid dopant with the thermally-cured dense polyaniline substrate, whereupon metal nanostructure deposits are formed on the doped substrate, wherein the deposits have a morphology which is dependent upon the acid dopant.

9. The method of claim 8, wherein the acid dopant is selected from the group consisting of tartaric acid, camphosulfonic acid, phosphoric acid, citric acid, mandelic acid, poly(styrene sulfonic acid), para-toluenesulfonic acid, and combinations thereof.

10. The method of claim 8, wherein the nanostructure deposits are sheets, cubes, spheres, needles, rods, or wires.

11. A method of performing surface-enhanced Raman spectral analysis of an analyte comprising:
    a) providing a a thermally-cured dense polyaniline substrate, wherein a surface of the substrate comprises metal nanostructure deposits and an acid dopant;
    b) bringing an analyte into effective contact with said metal-PANI composite;
    c) illuminating the metal-PANI composite with radiation of at least one wavelength for causing elemental-state particles to produce a plasmon field and for causing said plasmon field to interact with molecules of said analyte, in such a manner, so as to produce Raman photons; and,
    d) collecting scatted radiation emitted from said metal-PANI composite for spectral analysis.

12. The method of claim 11, wherein the metal is selected from the group consisting of silver and gold.

13. The method of claim 11, wherein the acid dopant is selected from the group consisting of tartaric acid, camphosulfonic acid, phosphoric acid, citric acid, mandelic acid, poly(styrene sulfonic acid), para-toluenesulfonic acid, and combinations thereof.

14. The method of claim 11, wherein the nanostructure deposits are sheets, cubes, spheres, needles, rods, or wires.

* * * * *